United States Patent [19]

Steinberg et al.

[11] 4,395,909
[45] Aug. 2, 1983

[54] BODY IMAGING TECHNIQUE

[75] Inventors: Bernard D. Steinberg, Wyndmoor; Earl N. Powers, Philadelphia, both of Pa.

[73] Assignee: Imaging Associates, Villanova, Pa.

[21] Appl. No.: 237,096

[22] Filed: Feb. 23, 1981

[51] Int. Cl.³ .............................................. G01N 29/04
[52] U.S. Cl. ......................................... 73/602; 73/606; 128/660
[58] Field of Search ................. 73/602, 606, 625, 626, 73/628; 128/660

[56] References Cited

U.S. PATENT DOCUMENTS 3,953,822  4/1976  Vilkomerson ........................ 73/602
4,074,564  2/1978  Anderson ............................. 73/602

Primary Examiner—Anthony V. Ciarlante
Attorney, Agent, or Firm—Weiser & Stapler

[57] ABSTRACT

An array of acoustic receiving transducers is placed next to the body to be imaged. Acoustic energy is initially projected through the body, picked up by these receiving transducers, and processed to determine any time domain deviations which exist in the paths actually followed by that energy from those paths which would have been followed if the body were substantially homogeneous and the transducer array substantially fixed. Further acoustic energy is also picked-up by the transducers, after reflection within the body to be imaged. The image of any given point within the body is then formed by selecting from each transducer output signal that portion which corresponds to the image forming energy emanating from that point, as corrected in accordance with the previously determined deviations.

11 Claims, 1 Drawing Figure

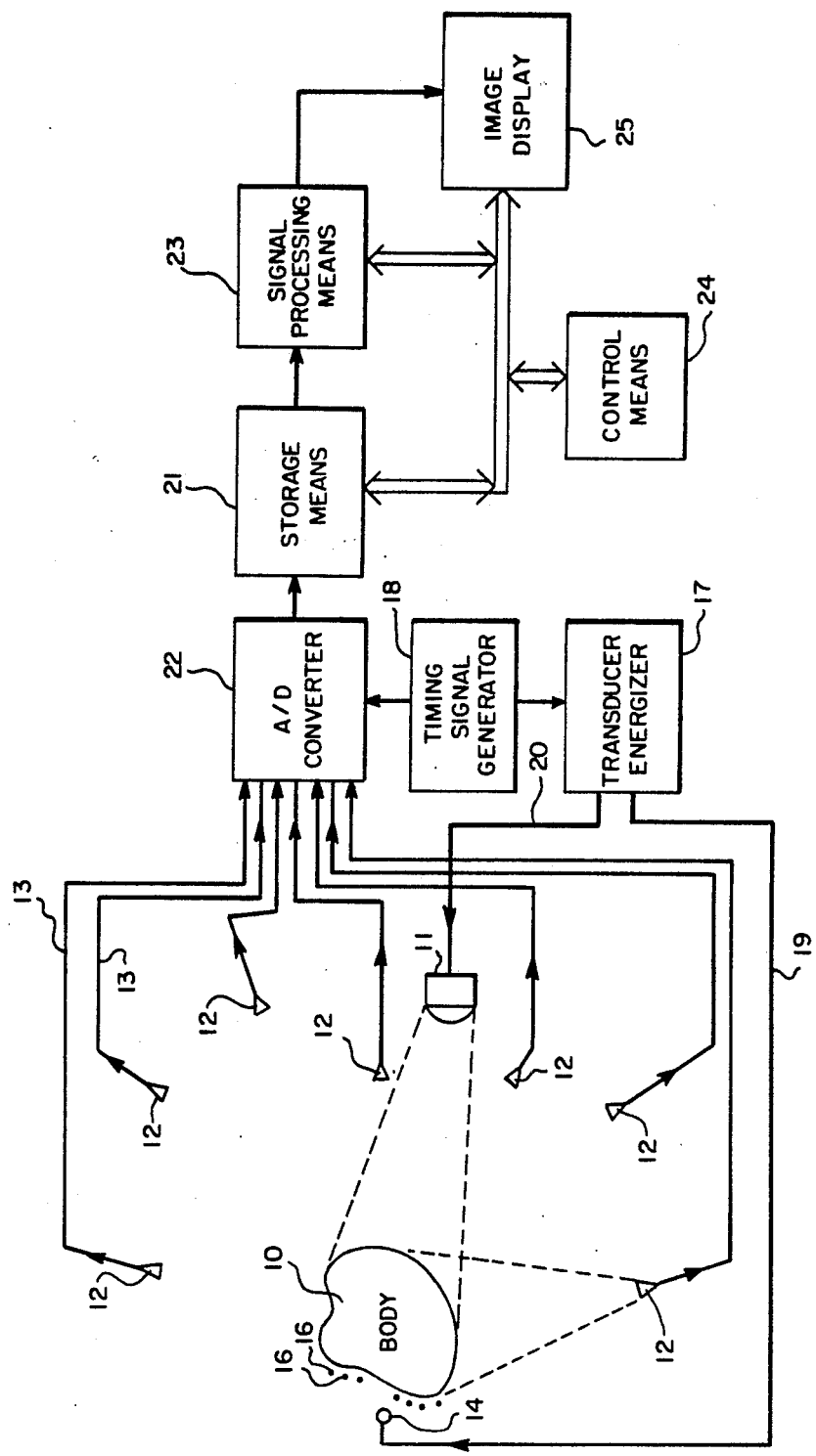

BODY IMAGING TECHNIQUE

The present invention relates to improvements in forming images of objects, or portions of objects, which are not accessible to conventional methods of optical observation.

Although not limited thereto, the invention is particularly applicable to forming such images of the interior of the human body.

It is known to carry out such image forming by the use of a plurality of ultrasonic transducers, which are positioned adjacent the body portion to be imaged in a predetermined geometric array. Coherent ultrasonic radiation is projected into the body, and the reflections picked up by the transducers. By signal processing of the transducer outputs, it is possible to produce electronically an image of a particular region within the irradiated body portion.

A particular embodiment of this known technique is disclosed in U.S. Pat. No. 3,953,822, issued Apr. 27, 1976. The embodiment there disclosed is quite sophisticated. It utilizes a relatively small number of transducers to provide a given resolution in the image which is ultimately formed. This is not only desirable in itself, but it also has the further desirable effect of reducing the complexity of the electronic circuitry which is used to process the output signals from these transducers.

On the other hand, there are other highly desirable features which that previously disclosed embodiment does not possess.

For example, in that previously disclosed embodiment, the geometric relationship between the transducers is strictly predetermined and the success of the technique is predicated on that particular geometry. This severely limits the usefulness of the embodiment. Different portions of the human body (leg, chest, shoulder, etc.) have widely varying shapes, and it would be highly desirable to be able to conform the array of transducers at will to the body shape in the area to which the array is being applied. For example, to wrap the transducer array at least partially around a leg, or to drape it over a shoulder, as may be indicated by the body portion to be examined, would be highly desirable.

As another illustration of the limitations of the previously disclosed embodiment under discussion, there is the matter of variations within the body tissues, which constitute the propagation medium for the acoustic energy used. In the previously described embodiment of U.S. Pat. No. 3,953,822, it can be shown that success is predicated on the assumption that this propagation medium has substantially uniform properties in the paths followed by the acoustic energy traveling to the transducer array. In practice, this is, of course, far from so, and distortions in image formation result.

As a final illustration, there is the matter of speed of observation. As explained in U.S. Pat. No. 3,953,822, the embodiment described therein requires several seconds to make a single "exposure" needed to form a given image of the body interior. Different images at varying distances from the array require separate such exposures. While this speed may be satisfactory for body tissues which remain stationary, it is too slow for observations of body tissues which move rapidly and/or unpredictably, such as the heart, stomach, intestines, etc. Also, in the previously described embodiment, in order to obtain images taken from different angles, the array must be moved to different positions. This further slows the observation process.

Accordingly, it is a primary object of the present invention to provide an improved technique for forming images of objects which are not conveniently accessible to conventional methods of optical observation.

It is another object to provide such an improved technique which is particularly suitable for use on body tissues.

It is still another object to provide such a technique which utilizes acoustic energy.

It is still another object to provide such a technique which overcomes one or more shortcomings of the prior art.

It is still another object to provide such a technique which requires only a single exposure to provide images from varying distances within the object under observation.

It is still another object to provide such a technique which requires only a single exposure to provide images which appear to have been taken from various angles.

These and other objects which will appear are achieved in accordance with the present invention as follows.

An array of receiving transducers is positioned in the vicinity of the body to be observed.

Acoustic energy is initially projected through the object so as to be picked up by these receiving transducers. This initially projected energy will be referred to as "synthetic beam forming energy." The signals which are produced by the transducers in response to that picked-up beam forming energy are processed so as to determine what deviations, if any, exist in the paths followed by that energy from those paths which would have been followed if the observed body were substantially homogeneous. In particular, such deviations in the time domain are determined.

After this synthetic beam forming energy has been picked-up, for processing as described above, it is replaced with the projected acoustic energy, also to be picked-up by the transducers, either after passage through, or more typically, after reflection within the interior of the body. This will be referred to as the "image forming energy".

A synthetic image can then be formed of any given point within the observed body by selecting from each of the signals produced by each of the transducers in the array that portion which corresponds to the image forming energy emanating from that point, and combining the so-selected portions.

The signal processing which is used for the above-mentioned selecting and combining utilizes the determination of deviations in the time domain which had previously been made by signal-processing in response to the synthetic beam forming energy. The deviation so determined for each transducer is used to compensate the transducer output signal so that the selected portions are closer to those which emanate from the desired point within the observed body.

The accuracy of this technique becomes progressively less as the location of the point within the body which it is desired to synthetically image becomes more and more remote from the focus point of the synthetic beam.

This accuracy decrease can be overcome, in accordance with the present invention, by forming auxiliary synthetic beams as needed, utilizing passive reflectors at known locations. Each auxiliary synthetic beam is then used to determine the appropriate time domain deviations for image points in its vicinity and to provide the necessary correction based thereon when forming the synthetic images of these points.

The present invention preferably contemplates that all the output signals from all the transducers in the array will be stored initially. All signal processing will then be performed using this stored information. In this manner, the body being observed will be subjected to the acoustic energy used for only a very brief time, typically a fraction of a second. This prevents the operation from becoming burdensomely time consuming, and also prevents body movements from distorting the observation. Image formation can then proceed at leisure, and can even take place at times and locations which are arbitrarily remote from the initial body observation.

For further details, reference is made to the discussion which follows, in light of the accompanying drawings wherein, the single FIGURE shows a diagrammatic illustration of an embodiment of the invention.

Referring to the drawing, this shows a body 10, which is to be observed in accordance with the present invention.

A transmitting transducer 11 projects ultrasonic acoustic energy onto the body 10. A plurality of receiving transducers 12 receive such acoustic energy from body 10 and transform it into corresponding electrical signals appearing on transducer output leads 13. Seven such receiving transducers 12 have been illustrated in the drawing, but it will be understood that a larger number will typically be involved. From practical consideration of image resolution, it appears at present that approximately one hundred receiving transducers would be used in typical applications of the invention to the imaging of human internal organs.

An additional transmitting transducer 14 is positioned on the opposite side of the body from receiving transducers 12. This transducer 14 is used for the initial synthetic beam forming, as more fully explained later. In addition, small objects 16, which strongly reflect acoustic energy, are distributed over the same side of the body on which transducer 14 is located. As is also explained later, those objects 16 are used for forming auxiliary synthetic beams.

Transmitting transducers 11 and 14 are both energized to emit coherent ultrasonic radiation by means of energizer 17. Under the control of timing signal generator 18, transducer 14 is energized first via connection 19, and then deenergized, while transducer 11 is then energized via connection 20. The acoustic energy is produced at conventional ultrasonic frequency, e.g. between 1.0 and 15 MHz.

The signal wave forms produced by all receiving transducers 12 in response to this consecutive energizing of transmitting transducers 14 and 11 are supplied to a storage means 21. Preferably, and as indicated in FIG. 1, these wave forms are supplied in the form of digital information, derived from the transducers output signals by A/D converter 22.

The rate of A/D conversion is preferably such that a great many more samples of each signal waveform are taken than the minimum number which is theoretically necessary to capture the information content. Thus, if a sampling rate of X is the theoretical minimum, a sampling rate of several times X, e.g. 20X is preferably used.

The transmitting transducer 14 is energized for a period of time which is sufficient to permit a train of ultrasonic waves to be created whose length (in space) spans the distance within which that transducer can be accurately located. Under practical conditions this may be about 1 cm. The transmitting transducer 11 is then energized for a period of time which is sufficient to permit a train of ultrasonic waves to be created whose length (in space) spans the thickness of the body under observation. This may typically be about 10 cm.

Assuming an ultrasonic frequency of 1 MHz, an appropriate sampling rate would be 40 MHz. The appropriate duration of the transmission from transducer 14 would be such that 400 samples are produced from the corresponding output signals of transducers 12, and the appropriate duration of the subsequent transmission from transducer 11 would be such that 5320 samples are produced from the corresponding output signals of transducer 12.

The digital signals representing these sampled values of the transducer output signals are all stored in storage means 21, which is preferably a rapid access RAM (random access memory) of adequate storage capacity. Specifically this RAM 21 must have storage capacity for 400 "numbers" from each receiving transducer 12 due to acoustic energy from transmitting transducer 14, and for 5320 "numbers" from each receiving transducer 12 due to acoustic energy from transmitting transducer 11.

Stored "numbers" from RAM 21 can be selectively supplied to signal processing means 23, under the control of control means 24. From this signal processing means, in turn, signals can be supplied to image display means 25, also under the control of control means 24.

Specifically, there are first drawn from RAM 21 the 400 numbers there stored as a result of reception by each transducer 12 of the energy from synthetic beam forming transducer 14. Each set of these 400 numbers is examined to determine the largest positive number in the set, and also the number following that largest number adjacent to which the sign changes from positive to negative. The deviation of that transition from a reference position within the sequence of 400 numbers, e.g. from the middle (position 200), is taken to indicate the actual time domain delay experienced at each receiving transducer 12 during passage of the acoustic energy through the observed body. The reference position is that position which corresponds to the time at which the acoustic energy is expected to arrive at the receiving transducer 12, as determined from accurately known locations of transducers 12 and 14 in the absence of body 10. Variations in the location of that transition, as between the number sets from different receiving transducers 12, represent actual deviations in this delay due to nonhomogeneities in the medium and/or irregularities in positioning of the receiving transducers 12.

These measurements of the different actual time delays can be regarded as constituting the forming of a synthetic receiving beam focused at transducer 14.

These measurements are next used to, in effect, produce synthetic receiving beams focused at other locations within the observed body, and in the vicinity of the location of transducer 14.

For example, the 5320 numbers stored from one receiving transducer 12 (e.g. the top-most one in the drawing) are first shifted in position within their stored sequence in storage means 21 by an amount corresponding to the deviation from reference of the transition previously determined to prevail for the 400 synthetic beam forming numbers from that same receiving transducer (the top-most one in the drawing).

The corresponding operation is performed for each of the other sets of 5320 numbers stored from the various receiving transducers 12, but using in each case the position shift determined by the deviations from reference of the transition in the set of 400 synthetic beam forming numbers from that same transducer 12.

In effect, this position shift aligns in the time domain all the receiving transducer output signals obtained in response to acoustic energy projected by transducer 11 by reflection from points in the observed object close to transducer 14, and taking into account the actual physical conditions which prevail inside the observed body, as well as in the positioning of the receiving transducers 12.

The synthetic image of any point within the observed body—at least in the vicinity of transducer 14—can now be obtained as follows.

Each of the sets of 5320 numbers, aligned as previously described, is examined within the same predetermined limited range of positions, to determine the location of the positive-to-negative transition adjacent to the largest positive number. This transition is taken to denote the position of the signal from the selected image point within each set of 5320 numbers. The absolute magnitudes of a predetermined quantity of numbers closely adjacent to the so-determined transition in all the number sets are then added, and the result represents the intensity of the acoustic image of the selected points.

The corresponding operation can be performed for other selected points within the observed body, by simply moving to a different range of positions within all the sets of 5320 numbers, and again going through the procedure described above, including transition identification, and addition of selected numbers.

As previously noted, the accuracy with which the alignment of the sets of 5320 numbers (which alignment is obtained by means of the synthetic beam formed with the use of transducer 14) can be used to form images of points within the observed object decreases as the separation between those images points and the transducer 14 increases. Reflectors 16 are provided to cope with this phenomenon.

Specifically, before obtaining the synthetic image of any point in the vicinity of one of these reflectors 16, that reflector is used, in a manner somewhat similar to the way in which transducer 14 was used, to refocus the synthetic beam at the location of that particular reflector 16.

For that purpose, there are selected a subset of 400 numbers from each receiving transducer output set of 5320 numbers, which subset includes the number corresponding to reflection from reflector 16. These subsets are then processed in a manner similar to the 400 numbers derived initially in response to synthetic beam forming transducer 14.

Thereafter, it is the time domain corrections derived from the various reflectors 16 which are used to appropriately shift the positions of the sets of 5320 numbers when determining the image points in their respective vicinities.

To display the image points so obtained, each one is identified with a given set of geometric coordinates corresponding to the same point within the observed body and, based on this identification, is displayed electronically on a cathode ray tube screen.

It is apparent that, by appropriate selection of individual image points, an over-all image of essentially any portions of the observed body can be displayed on display means 25.

The individual components which make up the over-all system in the drawing may be, in themselves, of entirely conventional form.

Thus, the transducers 11, 12 and 14 are all entirely conventional electro-acoustic components. For use in the present invention, they may be held in the desired array configuration by being embedded in a suitable mounting, such as a flexible rubber sheet, for example. This enables them to be applied directly to the surface which encloses the body to be observed, and also to conform to the shape of that surface. In this way, intimacy of acoustic coupling with the observed body is desirably promoted.

The reflectors 16 are also entirely conventional components. They may take the form of small bodies whose acoustic reflection properties differ sharply from those of the observed body. If that body is a human organ, for example, then reflectors 16 may be small steel bodies, embedded in the same flexible sheet which constitutes the mounting for the transducers 11, 12 and 14.

Transducer energizer 17 may be a conventional oscillator, and timing signal generator 18 may be a conventional circuit capable of turning the oscillator 17 on and off, and directing its output either to lead 19 or to lead 20, as well as of controlling the operation of A/D converter 22 so as to function in proper timing coordination with oscillator 17.

The A/D converter 22 itself may also be of conventional form, operating at the rates previously indicated. This may require connecting several individual A/D converters in parallel in known manner.

The storage means 21 may likewise be of conventional form. As previously discussed, this storage means must be capable of storing the digital signals produced by A/D converter 22, and of supplying them from storage to signal processing means 23.

The signal processing means 23 may also be of conventional form for performing the specific signal processing operations previously described. All of those operations will be readily recognized to be entirely conventional, in themselves. For example, the determination of which number within a sequence of numbers is the greatest is a conventional procedure in digital signal processing. The same applies to the determination of a change in sign of the numbers in question, the addition of their absolute magnitudes, and so forth.

The control means 24 which causes all this to happen is also completely conventional in digital technology. It will include a pre-programmed sequence of control functions to activate the various sequential processes within the signal processing means 23, and the suppling of the input signals necessary for the purpose from storage means 21. It will also provide the information concerning the relationships between the geometric coordinates of the transducer locations and the body points, and between these body points and the image display points, which determines the visible pattern in which any given selection of body image points is displayed as a complete image by use of image display means 25. This information may be provided by suitable conventional storage means, such as a magnetic disc memory.

Finally, the image display 25 may be of conventional form, e.g. a cathode ray tube display on whose CRT screen there is formed an image whose intensity (brightness) varies in accordance with variations in the image intensity of the various body points being displayed.

Numerous modifications of the specific embodiment described above are also possible without departing from the scope of the present invention.

For example, the frequency of the acoustic energy used can be varied within wide limits, the rate at which the A/D conversion takes place can be varied, and so can the number of quantization levels and resulting bits in the number-representative digital signals which result.

The number of receiving transducers used can be varied and so can their positions within the array formed by them.

The locations of the reflectors 16 can be varied. For example, if especially high precision of image formation is required deep within the body to be observed, then it may be desirable to correspondingly position one or more such reflectors so that accurate refocussing of the synthetic beam can be carried out at these deep positions. This may be achieved, for example, by injecting the necessary small reflector objects into the body to be observed.

Moreover the passive reflectors 16 can be replaced by active transducers similar to transmitting transducer 14, which are then energized at the re-focusing times.

Likewise, active transmitting transducer 14 can be replaced by a passive reflector 16, used for focusing in the manner which was originally described for re-focusing using reflectors 16.

A simplified way may be used to perform the re-focusing if the re-focusing points are close enough together so that the error in the alignment of the sets of 5320 numbers is small. This simplified way requires only determining the location of the sign transition adjacent to the center of the previously determined limited range of positions in each set of 5320 numbers. It is expected that determining of the transition location will require examination of a sub-set of numbers substantially smaller than 400. Having determined these transition locations, the re-focusing proceeds as previously described.

The signal processing need not necessarily be carried out on a digital basis. Analog signal processing can be used instead, and so forth.

We claim:

1. A system for producing signals, which can be used to form images of selected points within a body, comprising:
    means for initially projecting acoustic wave energy upon said body;
    means for further projecting acoustic wave energy upon said body;
    means for receiving said initially projected energy and said further projected energy after passage through the body at a plurality of transducers;
    means for firstly processing the signals produced by said transducers in response to said initially projected energy to determine deviations from reference conditions in the paths followed within the body by said initially projected energy to said transducers and for secondly
    processing the signals produced by said transducers in response to said further projected energy to form a signal representative of the image of at least one selected point within the body; and
    means for utilizing said deviation determinations to control the second signal processing so as to compensate for said deviations in the forming of the selected point image.

2. The system of claim 1 wherein
   the transducers are positioned in an array generally on one side of the body, and the initial wave energy projecting means is positioned on the opposite side of the body.

3. The system of claim 2 wherein
   the further wave energy projecting means is positioned on the same side of the body as the transducer array.

4. The system of claim 3 wherein
   the transducer array is adapted to assume a configuration which substantially conforms to the adjacent surface of the body.

5. The system of claim 2 wherein
   the signal processing means include means for forming a synthetic beam focused upon the means for initially projecting energy, and further include means for utilizing said synthetic beam to form the image representative signal.

6. The system of claim 5 further comprising
   means for refocusing the synthetic beam upon at least one location different from that of the initial projecting means.

7. The system of claim 6 wherein the refocusing means includes means for reflecting acoustic energy projected from said further energy projecting means.

8. The system of claim 1 wherein the utilizing means includes means for displacing in the time domain the signals produced by the second processing from any one transducer, in accordance with time domain deviations from reference of the signals produced by the first processing from the same transducer.

9. The system of claim 8 wherein
   the signal processing means includes means for accumulating those portions of the signals from all transducers having positions in the time domain after said compensation, corresponding to the selected point within the body.

10. The system of claim 9 further comprising
    means for visibly displaying said accumulated signals.

11. The method of producing signals, which can be used to form images of selected points within a body, comprising:
    initially projecting acoustic wave energy upon said body;
    further projecting acoustic wave energy upon said body;
    receiving at a plurality of transducers said initially projected energy and said further projected energy after passage through the body;
    processing the signals produced by said transducers in response to said initially projected energy to determine deviations from reference conditions in the paths followed by said initially projected energy to said transducers;
    processing the signals produced by said transducers in response to said further projected energy to form a signal representative of the image of at least one selected point within the body; and
    utilizing said deviation determinations to control the second signal processing so as to compensate for said deviations in the forming of the selected point image.

* * * * *